United States Patent
Benattar et al.

(10) Patent No.: US 11,208,425 B2
(45) Date of Patent: Dec. 28, 2021

(54) PROCESS FOR PREPARING POLYOL GLYCOSIDES

(71) Applicant: SOCIETE D'EXPLOITATION DE PRODUITS POUR LES INDUSTRIES CHIMIQUES SEPPIC, Paris (FR)

(72) Inventors: Andre Benattar, Castres (FR); Andrey Bonnardel, Castres (FR); Jerome Guilbot, Castres (FR); Sebastien Kerverdo, Vincennes (FR); Herve Rolland, Castres (FR); Guy Tabacchi, Paris (FR)

(73) Assignee: SOCIETE D'EXPLOITATION DE PRODUITS POUR LES INDUSTRIES CHIMIQUES SEPPIC, Paris (FR)

( * ) Notice: Subject to any disclaimer, the term of this patent is extended or adjusted under 35 U.S.C. 154(b) by 267 days.

(21) Appl. No.: 15/900,544

(22) Filed: Feb. 20, 2018

(65) Prior Publication Data
US 2018/0170956 A1    Jun. 21, 2018

Related U.S. Application Data

(62) Division of application No. 14/780,906, filed as application No. PCT/FR2014/050197 on Feb. 4, 2014, now abandoned.

(30) Foreign Application Priority Data

Mar. 26, 2013    (FR) ...................................... 1352693

(51) Int. Cl.
| | | |
|---|---|---|
| *A61K 8/60* | (2006.01) | |
| *A61Q 1/14* | (2006.01) | |
| *A61Q 5/02* | (2006.01) | |
| *A61Q 19/10* | (2006.01) | |
| *A61Q 19/00* | (2006.01) | |
| *A61Q 19/04* | (2006.01) | |
| *A61Q 19/08* | (2006.01) | |
| *A61Q 17/04* | (2006.01) | |
| *C07H 15/04* | (2006.01) | |
| *C07D 493/04* | (2006.01) | |
| *C07H 1/00* | (2006.01) | |
| *C07D 307/20* | (2006.01) | |

(52) U.S. Cl.
CPC ............. *C07H 15/04* (2013.01); *A61K 8/602* (2013.01); *A61Q 1/14* (2013.01); *A61Q 5/02* (2013.01); *A61Q 19/10* (2013.01); *C07D 307/20* (2013.01); *C07D 493/04* (2013.01); *C07H 1/00* (2013.01); *A61Q 17/04* (2013.01); *A61Q 19/00* (2013.01); *A61Q 19/04* (2013.01); *A61Q 19/08* (2013.01)

(58) Field of Classification Search
CPC . A61K 8/602; A61Q 1/14; A61Q 5/02; A61Q 19/00; A61Q 19/04; A61Q 19/08; A61Q 19/10; A61Q 17/04
See application file for complete search history.

(56) References Cited

U.S. PATENT DOCUMENTS

| | | |
|---|---|---|
| 3,346,558 A | 10/1967 | Deane |
| 3,772,269 A | 11/1973 | Lew |
| 4,024,290 A | 5/1977 | Layton |
| 2009/0258808 A1 | 10/2009 | Roso et al. |
| 2011/0046365 A1* | 2/2011 | Mikkonen ................. C08B 3/22 536/68 |

FOREIGN PATENT DOCUMENTS

| | | |
|---|---|---|
| EP | 0 077 167 A1 | 4/1983 |
| EP | 0 092 875 A1 | 11/1983 |
| EP | 0 570 056 A1 | 11/1993 |
| FR | 2 898 810 A1 | 9/2007 |
| JP | 2009-534300 A | 9/2009 |
| JP | 2011-057610 A | 3/2011 |
| WO | 2007/110526 A2 | 10/2007 |

OTHER PUBLICATIONS

International Search Report, dated Apr. 3, 2014, from corresponding PCT application No. PCT/FR2014/050197.
FR Search Report, dated Sep. 10, 2013, from corresponding FR application No. 1352693.

* cited by examiner

*Primary Examiner* — Bahar Craigo
(74) *Attorney, Agent, or Firm* — Nixon & Vanderhye

(57) ABSTRACT

A process for preparing a composition ($C_1$) represented by the formula (I): HO—$CH_2$—$(CHOH)_n$—$CH_2$—O-$(G)_x$-H, in which G represents the remainder of a reducing sugar, n is an integer equal to 2, 3 or 4 and x, which indicates the mean degree of polymerization of the remainder G, represents a decimal number greater than 1 and less than or equal to 5, characterized in that the process includes at least one step a) of reacting a polyol of formula ($A_1$): HO—$CH_2$—$(CHOH)_n$—$CH_2$—OH, in which n is an integer equal to 2, 3 or 4, with a reducing sugar of formula (II): HO-G-H, in which G represents the remainder of a reducing sugar, in the presence of an acid catalyst ($C_a$), and in that the acid catalyst ($C_a$) is chosen from phosphorous acid, phosphoric acid and polyphosphoric acid.

8 Claims, No Drawings

PROCESS FOR PREPARING POLYOL GLYCOSIDES

The invention relates to a novel process for the preparation of polyol glycosides and to novel compositions based on polyol glycosides resulting from such a process.

The invention has applications mainly in the fields of cosmetics, dermocosmetics, pharmaceuticals and dermopharmaceuticals but also in the field of food, such as for example, as sweetener and/or bulk sweetener, in the field of the textile industry, for example for the treatment of woven or knitted synthetic or natural textile fibers, or also in the field of the paper industry, for example for the manufacture of paper for sanitary or domestic use.

Polyol glycosides can be prepared by reacting a polysaccharide, such as starch, with a polyol, such as a linear or branched aliphatic compound comprising from two to twenty carbon atoms and comprising at least two hydroxyl groups. These processes are generally carried out under high pressure conditions at a temperature generally greater than or equal to 120° C., in the presence of at least one acid catalyst. The polysaccharide is hydrolyzed to given an oligosaccharide and a monosaccharide which react with the polyol according to an acetalization reaction to form polyol glycosides.

The United States patent published under the number U.S. Pat. No. 3,346,558 more particularly discloses a continuous process for the preparation of polyol glycosides employing starch and an aliphatic polyol comprising from two to six hydroxyl groups, at a temperature of between 170° C. and 300° C. and under a pressure greater than the vapor pressure of the reaction mixture, in the presence of an acid catalyst and more particularly of a sulfonic acid or of a Lewis acid.

However, these processes have operating conditions which consume a great deal of energy, the polyol glycosides obtained exhibit a poorly controlled glycoside structure and their color, which is often dark, renders them unsuitable for uses in preparing cosmetic and/or pharmaceutical compositions.

Polyol glycosides can also be prepared by reacting a reducing sugar having a better-defined structure, such as a monosaccharide, with a polyol as described above, according to an acetalization reaction under moderate temperature conditions, generally between 70° C. and 130° C., at atmospheric pressure or under reduced pressure, generally between $3 \times 10^4$ Pa (300 mbar) and $2 \times 10^3$ Pa (20 mbar), and in the presence of an acid catalytic system generally chosen from strong inorganic acids, strong organic acids, carboxylic acids, Lewis acids and ion-exchange resins.

The United States patent published under the number U.S. Pat. No. 4,024,290 discloses the preparation of glucosyl sorbitol by reaction between glucose and sorbitol, at a temperature of 160° C., under reduced pressure, in the presence of an ion-exchange resin of acid type. Such a process makes it possible to predominantly obtain glucosyl sorbitol, the product of the acetalization reaction of sorbitol with glucose, and also residual sorbitol and byproducts.

The United States patent published under the number U.S. Pat. No. 3,772,269 discloses that the acetalization reactions of aliphatic glycols with reducing sugars are carried out in the presence of strong inorganic acids, such as hydrochloric acid, sulfuric acid, phosphoric acid or phosphorous acid, or of Lewis acids, such as boron trifluoride, of strong organic acids, such as para-toluenesulfonic acid, or ion-exchange resins, sulfuric acid being regarded as the preferred catalyst as a result of its ease of removal on conclusion of the acetalization reaction.

However, the use of such catalytic systems exhibits the twofold disadvantage of promoting the formation, in undesired amounts, of polyglucoses and of achieving highly colored reaction products.

In order to overcome these two problems, a person skilled in the art can carry out an acetalization reaction by direct reaction of a reducing sugar and of an excess of alcohol, in the presence of an acid catalytic system, followed by a stage of distillation of the residual fatty alcohol and, if necessary, followed by a stage of decoloration by addition of aqueous hydrogen peroxide solution under predetermined pH conditions.

Another complementary approach consists in employing specific catalytic systems. The European patent application published under the number EP 0 570 056 A1 describes the preparation of alkyl polyglucosides by acetalization of glucose with fatty alcohols in the presence of a catalytic system formed by a strong organic acid, selected from the group consisting of alkylbenzenesulfonic acids and secondary or tertiary alkanesulfonic acids, and a weak organic base having a Ka value of between $10^{-8}$ and $10^{-1}$ which is selected from pyridine, picolines, lutidines, collidines, quinolines, isoquinoline, quinaldine, pyrazine, pteridine and N,N,N',N'-tetramethylurea.

The European patent application published under the number EP 0 077 167 A describes a process for producing alkyl glycosides from monosaccharides and linear or branched alcohols comprising at least 10 carbon atoms, in the presence of an acid catalytic system composed of an acid catalyst and a reducing agent. The acid catalysts employed in such a process are the acid catalysts known to a person skilled in the art, such as, for example, sulfuric acid, hydrochloric acid, nitric acid, sulphonic acids, such as, for example, methanesulfonic acid, para-toluenesulfonic acid or trifluoromethanesulfonic acid, and strong acid ion-exchange resins; the reducing agents employed in such a process are chosen from phosphorous acid, hypophosphorous acid, sulfurous acid, hyposulfurous acid, nitrous acid and hyponitrous acid.

This state of the art associated with the preparation of alkyl polyglycosides is commonly transposed for the preparation of polyol glycosides. Thus, the international application published under the number WO 03/094864 discloses the preparation of polyol glycosides by acetalization of a reducing sugar and a polyol of formula ($A_1$):

$$HO—CH_2—(CHOH)_n—CH_2—OH \qquad (A_1)$$

in which n is an integer equal to 2, 3 or 4, in the presence of an acid catalytic system chosen from sulfuric acid, hydrochloric acid, phosphoric acid, nitric acid, hypophosphorous acid, methanesulfonic acid, para-toluenesulfonic acid, trifluoromethanesulfonic acid and acid ion-exchange resins, and more particularly the preparation of xylityl glucoside and erythrityl glucoside by the reaction of glucose with the corresponding polyols in the presence of an acid catalytic system composed of sulfuric acid.

While the choice of such catalytic systems makes it possible to increase the conversion of the polyol to polyol glucoside, the formation is observed, however, of byproducts resulting from the dehydration of the polyol of formula ($A_1$) in an acid medium, resulting in the formation of cyclic derivatives of said polyol of formula ($A_1$).

Thus:
when the polyol of formula ($A_1$) is erythritol (n=2), it dehydrates in an acid medium to give 3,4-dihydroxytetrahydrofuran of formula ($B_{11}$):

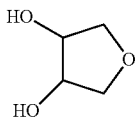
(B11)

when the polyol of formula ($A_1$) is xylitol (n=3), it dehydrates in an acid medium to give 3,4-dihydroxy-2-(hydroxymethyl)tetrahydrofuran of formula ($B_{12}$) (or 1,4-anhydroxylitol):

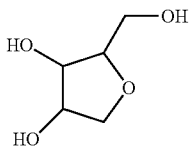
(B12)

when the polyol of formula ($A_1$) is sorbitol (n=4), it dehydrates in an acid medium to give 2-(1,2-dihydroxyethyl)-3,4-dihydroxytetrahydrofuran of formula ($B_{13}$) (or 1,4-anhydrosorbitol) and to give 1,5-dioxabicyclo[3.3.0]octane-3,7-diol of formula ($B_{14}$) (or isosorbide):

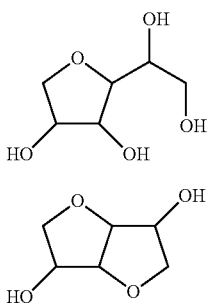
(B13)

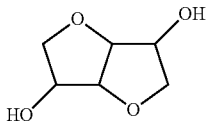
(B14)

The formation of these dehydration byproducts of the polyols of formula ($A_1$) competes with the acetalization reaction and does not make it possible to obtain a satisfactory yield for the formation of polyol glycosides.

The inventors have thus tried to develop a novel process which significantly minimizes the formation of the dehydration byproducts of the polyols of formula ($A_1$).

Thus, according to a first aspect, the subject matter of the invention is a process for the preparation of a composition ($C_1$) represented by the formula (I):

$$HO—CH_2—(CHOH)_n—CH_2—O-(G)_x-H \qquad (I),$$

in which G represents the residue of a reducing sugar, n is an integer equal to 2, 3 or 4 and x, which indicates the mean degree of polymerization of said residue G, represents a decimal number greater than 1 and less than or equal to 5, characterized in that said process comprises at least one stage a of reaction of a polyol of formula ($A_1$):

$$HO—CH_2—(CHOH)_n—CH_2—OH \qquad (A_1),$$

in which n is an integer equal to 2, 3 or 4, with a reducing sugar of formula (II):

$$HO\text{-}G\text{-}H \qquad (II)$$

in which G represents the residue of a reducing sugar, in the presence of an acid catalyst ($C_a$), and in that said acid catalyst ($C_a$) is chosen from hypophosphorous acid, phosphoric acid and polyphosphoric acid.

Polyphosphoric acid denotes the compounds of formula ($C_{a1}$):

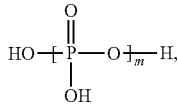
($C_{a1}$)

in which m represents a decimal number greater than 1 and less than or equal to 15, more particularly greater than or equal to 2 and less than or equal to 5 and more particularly still greater than or equal to 2 and less than or equal to 3.

Reducing sugar denotes, in the formulae (I) and (II) as defined above, saccharide derivatives which do not exhibit, in their structures, a glycoside bond established between an anomeric carbon and an oxygen of an acetal group as they are defined in the reference work "Biochemistry", Daniel Voet and Judith G. Voet, p. 250, John Wiley & Sons, 1990. The oligomeric structure $(G)_x$ can be provided in all forms of isomerisms, whether optical isomerism, geometric isomerism or positional isomerism; they can also represent a mixture of isomers.

$HO—CH_2—(CHOH)_n—CH_2—O\text{-}(G)_x\text{-}H$ means that said composition ($C_1$) is essentially composed of a mixture of compounds represented by the formulae ($I_1$), ($I_2$), ($I_3$), ($I_4$) and ($I_5$):

$$HO—CH_2—(CHOH)_n—CH_2—O\text{-}(G)_1\text{-}H \qquad (I_1),$$

$$HO—CH_2—(CHOH)_n—CH_2—O\text{-}(G)_2\text{-}H \qquad (I_2),$$

$$HO—CH_2—(CHOH)_n—CH_2—O\text{-}(G)_3\text{-}H \qquad (I_3),$$

$$HO—CH_2—(CHOH)_n—CH_2—O\text{-}(G)_4\text{-}H \qquad (I_4),$$

$$HO—CH_2—(CHOH)_n—CH_2—O\text{-}(G)_5\text{-}H \qquad (I_5),$$

in the respective molar proportions $a_1$, $a_2$, $a_3$, $a_4$ and $a_5$ such that the sum $a_1+a_2+a_3+a_4+a_5$ is equal to 1 and that each of the proportions $a_1$, $a_2$, $a_3$, $a_4$ and $a_5$ is greater than or equal to zero and less than or equal to one.

Essentially indicates, in the preceding definition, that the presence of one or more compounds of formula ($I_w$) with w greater than 5 is not ruled out within the composition ($C_1$) but that, if presence there is, it is in minimum proportions which do not result in any substantial modification of the properties of said composition ($C_1$).

In the formula (I) as defined above, the group:

$$HO—CH_2—(CHOH)_n—CH_2—O—,$$

is bonded to $(G)_x$ via the anomeric carbon of the saccharide residue, such as to form an acetal function group.

Stage a) of the process as defined above is carried out in a reactor by dispersion of the reducing sugar of formula (II) over the polyol of formula ($A_1$) brought beforehand to a temperature ($T_1$) greater by at least 5° C. than its melting temperature, with mechanical stirring. When said reducing sugar of formula (II) is homogeneously dispersed over said polyol of formula ($A_1$), said acid catalyst ($C_a$) is added and then the reaction medium thus prepared is maintained for a period of time of between 3 hours and 7 hours, under a partial vacuum of between 300 mbar ($3\times10^4$ Pa) and 20 mbar ($2\times10^3$ Pa), at a temperature ($T_2$) greater by at least 5° C. than the melting temperature of the polyol of formula ($A_1$).

When the polyol of formula ($A_1$) is xylitol or sorbitol, the temperature ($T_1$) is greater than or equal to 95° C. and less than or equal to 130° C. and more particularly greater than or equal to 95° C. and less than or equal to 115° C., while the temperature ($T_2$) is greater than or equal to 95° C. and less than or equal to 130° C. and more particularly greater than or equal to 105° C. and less than or equal to 120° C.

When the polyol of formula ($A_1$) is erythritol, the temperatures ($T_1$) and ($T_2$), which are identical or different, are greater than or equal to 120° C. and less than or equal to 135° C. and more particularly less than or equal to 130° C.

Stage a) of the process as defined above can be supplemented, if necessary or if desired, by subsequent operations of neutralization, for example with sodium hydroxide or with potassium hydroxide, and/or of filtration, and/or of decoloration, and/or of removal of the residual polyol, for example by selective extraction by means of a suitable solvent medium.

According to a specific aspect of the present invention, in the definition of the compounds of formulae (I) and (II), G represents the residue of a reducing sugar chosen from glucose, dextrose, sucrose, fructose, idose, gulose, galactose, maltose, isomaltose, maltotriose, lactose, cellobiose, mannose, ribose, xylose, arabinose, lyxose, allose, altrose, dextran or tallose.

According to another specific aspect of the present invention, in the definition of the polyol of formula ($A_1$), n is an integer equal to 2.

According to another specific aspect of the present invention, in the definition of the polyol of formula ($A_1$), n is an integer equal to 3.

According to another specific aspect of the present invention, in the definition of the polyol of formula ($A_1$), n is an integer equal to 4.

According to a specific aspect, a subject matter of the present invention is a process as defined above for which, in the definition of the compounds of formula (I) and of the compounds of formula (II), G represents the residue of a reducing sugar chosen from the residues of glucose, xylose and arabinose.

According to an even more specific aspect of the present invention, a subject matter of the present invention is a process as defined above, characterized in that, in the formula (I), x represents a decimal number greater than or equal to 1.05 and less than or equal to 3, more particularly greater than or equal to 1.15 and less than or equal to 2.5.

According to another specific aspect, a subject matter of the present invention is a process as defined above, characterized in that, in stage a), the molar ratio, of a reducing sugar of formula (II) to polyol of formula ($A_1$), is greater than or equal to ⅙ and less than or equal to 4/1, more particularly greater than or equal to ⅓ and less than or equal to 4/1, and more particularly still greater than or equal to ⅓ and less than or equal to 2/1.

According to another specific aspect, a subject matter of the present invention is a process as defined above, characterized in that, in stage a), the proportion by weight of acid catalyst ($C_a$) is greater than or equal to 0.05% and less than or equal to 2%, per 100% of the sum of the weights of a reducing sugar of formula (II) and of polyol of formula ($A_1$), more particularly greater than or equal to 0.1% and less than or equal to 1%, per 100% of the sum of the weights of a reducing sugar of formula (II) and of polyol of formula ($A_1$) and more particularly still greater than or equal to 0.2% and less than or equal to 1%, per 100% of the sum of the weights of a reducing sugar of formula (II) and of polyol of formula ($A_1$).

According to another specific aspect, a subject matter of the present invention is a process as defined above, characterized in that, in stage a), the acid catalyst ($C_a$) employed is hypophosphorous acid.

According to another specific aspect, a subject matter of the present invention is a process as defined above, characterized in that, in stage a), the acid catalyst ($C_a$) employed is phosphoric acid.

Another subject matter of the invention is a composition ($C_2$) comprising, per 100% of its weight:

from 1% to 70% by weight of a polyol of formula ($A_1$):

$$HO-CH_2-(CHOH)_n-CH_2-OH \quad (A_1),$$

in which n is an integer equal to 2, 3 or 4;

from 25% to 98.9% by weight of a composition ($C_1$) represented by the formula (I):

$$HO-CH_2-(CHOH)_n-CH_2-O-(G)_x-H \quad (I),$$

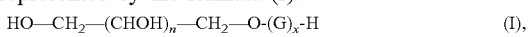

in which G represents the residue of a reducing sugar, n is an integer equal to 2, 3 or 4 and x, which indicates the mean degree of polymerization of said residue G, represents a decimal number of greater than 1 and less than or equal to 5;

from 0.1% to 5% by weight of a compound (B) or of a mixture of compounds (B) chosen from:
the compound of formula ($B_{11}$):

the compound of formula ($B_{12}$):

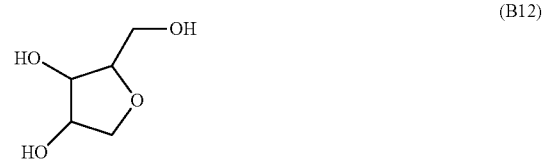

the compound of formula ($B_{13}$):

and the compound of formula ($B_{14}$):

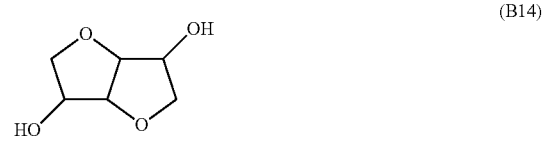

According to a specific aspect of the present invention, the composition ($C_2$) as defined above comprises, per 100% of its weight:
- from 5% to 65% by weight, more particularly from 10% to 60% by weight, of at least one polyol of formula ($A_1$),
- from 31% to 94.5% by weight, more particularly from 37% to 89.5% by weight, of at least one composition ($C_1$),
- from 0.5% to 4% by weight, more particularly from 0.5% to 3% by weight, of a compound (B) or of a mixture of compounds (B) chosen from the compounds of formulae ($B_{11}$), ($B_{12}$), ($B_{13}$) and ($B_{14}$).

According to another specific aspect, the composition ($C_2$) as defined above is characterized in that, in the formula (I), said residue G of a reducing sugar is chosen from the residues of glucose, dextrose, sucrose, fructose, idose, gulose, galactose, maltose, isomaltose, maltotriose, lactose, cellobiose, mannose, ribose, xylose, arabinose, lyxose, allose, altrose, dextran or tallose.

According to a more specific aspect, the composition ($C_2$) as defined above is characterized in that, in the formula (I), said residue G of a reducing sugar is chosen from the residues of glucose, xylose and arabinose and x represents a decimal number of greater than or equal to 1.05 and less than or equal to 3, more particularly of greater than or equal to 1.15 and less than or equal to 2.5.

According to another specific aspect, a subject matter of the invention is:
- either the composition ($C_2$) as defined above for which, in the formula ($A_1$), n is an integer equal to 2, in the formula (I), n is an integer equal to 2, said residue G of a reducing sugar represents the residue of glucose and x represents a decimal number of between 1.05 and 2.5, and the compound (B) is the compound of formula ($B_{11}$);
- or the composition ($C_2$) as defined above for which, in the formula ($A_1$), n is an integer equal to 3, in the formula (I), n is an integer equal to 3, said residue G of a reducing sugar represents the residue of glucose and x represents a decimal number of between 1.05 and 2.5, and the compound (B) is the compound of formula ($B_{12}$);
- or the composition ($C_2$) as defined above for which, in the formula ($A_1$), n is an integer equal to 4, in the formula (I), n is an integer equal to 4, said residue G of a reducing sugar represents the residue of glucose and x represents a decimal number of between 1.05 and 2.5, and the compound (B) is a mixture of the compound of formula ($B_{13}$) and the compound ($B_{14}$).

The composition ($C_2$) which is a subject matter of the invention can be obtained by different routes.

A first route for the preparation of the composition ($C_2$) consists, in a first stage $E_1$), in introducing at least one polyol of formula ($A_1$) as defined above, at least one composition ($C_1$) represented by the formula (I) as defined above and at least one compound of formula (B) as defined above into a reactor according to a controlled ratio by weight, under temperature conditions which make it possible to ensure the homogeneity of the mixture, preferentially between 60° C. and 120° C., then, if necessary or if desired, in a second stage $E_2$), in introducing a reducing sugar of formula (II) as defined above into the mixture obtained in stage $E_1$) and in continuing until a homogenous composition is obtained.

A second route for the preparation of the composition ($C_2$) consists, in a first stage $E_3$), in employing the process for preparation of the composition ($C_1$), which is a subject matter of the present invention, and then, if necessary or if desired, of subsequent stages of neutralization, of filtration and/or of decoloration.

According to a specific aspect, when the composition ($C_2$) which is a subject matter of the present invention is prepared according to the second preparation route, said composition ($C_2$) can additionally comprise a residual amount of the reducing sugar of formula (II) as defined above.

Such a residual amount of the reducing sugar of formula (II) is comprised, per 100% of the weight of the composition ($C_2$), of 0.1% to 10% by weight and more particularly of 0.1% to 4.0% by weight.

The composition ($C_1$) and composition ($C_2$) as defined above can be incorporated in any type of cosmetic, dermocosmetic, dermopharmaceutical or pharmaceutical formulation intended for topical use or else in any type of support intended to be brought into contact with the skin (paper, wipe, textile, transdermal device, and the like).

This is why, according to another aspect, a subject matter of the invention is the use of the composition ($C_1$), directly obtained by the process as defined above, or of the composition ($C_2$) as defined above, as constituent component of cosmetic, dermopharmaceutical or pharmaceutical formulations for topical use, in the preparation of said cosmetic, dermopharmaceutical or pharmaceutical formulations for topical use.

The expression "for topical use" used in the definition of the formulation in which said composition ($C_1$) or ($C_2$) can be incorporated means that said formulation is employed by application on the skin, hair, scalp or mucous membranes, whether it is a direct application in the case of a cosmetic, dermocosmetic, dermopharmaceutical or pharmaceutical formulation or an indirect application, for example in the case of a body hygiene, skincare or skin protection product provided in the form of an article made of textile, such as, for example, a wipe, or made of paper, such as, for example, a paper for sanitary use.

The cosmetic, dermocosmetic, dermopharmaceutical or pharmaceutical formulation intended for topical use in which said composition ($C_1$) or ($C_2$) can be incorporated are provided in particular in the form of an aqueous or oily solution, of an emulsion or of a microemulsion of the water-in-oil (W/O) or oil-in-water (O/W) type, of a multiple emulsion of water-in-oil-in-water (W/O/W) or oil-in-water-in-oil (O/W/O) type, of a gel, of a soap or of a syndet, of a balm, of a hydrodispersion, of a cream, of a foam or of an aerosol or also in anhydrous form, such as a powder.

These formulations can be used as cleansing or makeup-removing milks, as cleansing or makeup-removing lotions, as foaming gels for the face or for the body, as shampoo for cleaning the hair and/or scalp, as conditioner for the treatment of the hair and/or scalp, as foam bath, as cream, as milk or as lotion for caring for or protecting the face, hands and body, such as, for example, as agent for protecting from solar radiation, as self-tanning agent, as antiaging agent, as antiwrinkle agent, as soothing agent or as moisturizing agent.

Generally, these formulations are intended for topical use in which said composition ($C_1$) or ($C_2$) can be incorporated also comprise excipients and/or active principles habitually employed in the field of formulations for topical use, in particular cosmetic, dermocosmetic, pharmaceutical or dermopharmaceutical formulations, such as foaming and/or detergent surfactants, thickening and/or gelling surfactants, thickening and/or gelling agents, stabilizing agents, film-forming compounds, solvents and cosolvents, hydrotropic agents, plasticizing agents, fatty substances, oils and waxes, emulsifying and coemulsifying agents, opacifying agents, pearlescing agents, superfatting agents, sequestering agents, chelating agents, antioxidants, fragrances, essential oils, preservatives, conditioning agents, whitening agents intended for bleaching hairs and the skin, active principles intended to contribute a treating and/or protective action with regard to the skin or hair, sunscreens, pigments or inorganic fillers, particles which will provide a visual effect or which are intended for the encapsulation of active principles, exfoliating particles, texturing agents, optical brighteners or insect repellents.

Mention may be made, as examples of foaming and/or detergent surfactants which are optionally present in the formulations for topical use in which said composition ($C_1$) or ($C_2$) can be incorporated, of topically acceptable anionic, cationic, amphoteric or nonionic foaming and/or detergent surfactants habitually used in this field of activity.

Mention may be made, among the anionic foaming and/or detergent surfactants which can be combined with the formulations for topical use in which said composition ($C_1$) or ($C_2$) can be incorporated, of alkali metal salts, alkaline earth metal salts, ammonium salts, amine salts or aminoalcohol salts of alkyl ether sulfates, alkyl sulfates, alkylamido ether sulfates, alkylaryl polyether sulfates, monoglyceride sulfates, α-olefinsulfonates, paraffinsulfonates, alkyl phosphates, alkyl ether phosphates, alkylsulfonates, alkylamidesulfonates, alkylarylsulfonates, alkylcarboxylates, alkyl sulfosuccinates, alkyl ether sulfosuccinates, alkylamide sulfosuccinates, alkyl sulfoacetates, alkylsarcosinates, acylisethionates, N-acyltaurates, acyl lactylates, N-acylated derivatives of amino acids, N-acylated derivatives of peptides, N-acylated derivatives of proteins or fatty acids.

Mention may be made, among the amphoteric foaming and/or detergent surfactants which can be combined with the formulations for topical use in which said composition ($C_1$) or ($C_2$) can be incorporated, of alkyl betaines, alkyl amido betaines, sultaines, alkyl amidoalkyl sulfobetaines, imidazoline derivatives, phosphobetaines, amphopolyacetates and amphopropionates.

Mention may in particular be made, among the cationic foaming and/or detergent surfactants which can be combined with the formulations for topical use in which said composition ($C_1$) or ($C_2$) can be incorporated, of quaternary ammonium derivatives.

Mention may more particularly be made, among the nonionic foaming and/or detergent surfactants which can be combined with the formulations for topical use in which said composition ($C_1$) or ($C_2$) can be incorporated, of alkyl polyglycosides, castor oil derivatives, polysorbates, coconut amides or N-alkylamines.

Mention may more particularly be made, among the nonionic foaming and/or detergent surfactants which can be combined with the formulations for topical use in which said composition ($C_1$) or ($C_2$) can be incorporated, of the composition ($C_3$) or a mixture of compositions ($C_3$), said composition ($C_3$) being represented by the formula (IV):

$$R_2\text{—O-}(G_2)_p\text{-H} \qquad (IV)$$

in which $R_2$ represents a saturated or unsaturated and linear or branched aliphatic radical comprising from 8 to 14 carbon atoms, $G_2$ represents the residue of a reducing sugar and p represents a decimal number of greater than or equal to 1.05 and less than or equal to 5, said composition ($C_3$) being essentially composed of a mixture of compounds represented by the formulae ($IV_1$), ($IV_2$), ($IV_3$), ($IV_4$) and ($IV_5$):

$$R_2\text{—O-}(G_2)_1\text{-H} \qquad (IV_1),$$

$$R_2\text{—O-}(G_2)_2\text{-H} \qquad (IV_2),$$

$$R_2\text{—O-}(G_2)_3\text{-H} \qquad (IV_3),$$

$$R_2\text{—O-}(G_2)_4\text{-H} \qquad (IV_4),$$

$$R_2\text{—O-}(G_2)_5\text{-H} \qquad (IV_5),$$

in the respective molar proportions $a_1$, $a_2$, $a_3$, $a_4$ and $a_5$, such that the sum $a_1+a_2+a_3+a_4+a_5$ is equal to 1 and that each of the proportions $a_1$, $a_2$, $a_3$, $a_4$ and $a_5$ is greater than or equal to zero and less than or equal to one.

Mention may be made, as examples of thickening and/or gelling surfactants optionally present in the formulations for topical use in which said composition ($C_1$) or ($C_2$) can be incorporated, of optionally alkoxylated fatty esters of alkyl polyglycosides and very particularly ethoxylated esters of methyl polyglucoside, such as PEG-120 methyl glucose trioleate or PEG-120 methyl glucose dioleate, sold respectively under the names Glucamate™ LT and Glumate™ DOE120; alkoxylated fatty esters, such as PEG-150 pentaerythrityl tetrastearate, sold under the name Crothix™ DS53, or PEG-55 propylene glycol oleate, sold under the name Antil™ 141; or carbamates of polyalkylene glycols comprising fatty chains, such as PPG 14 laureth isophoryl dicarbamate, sold under the name Elfacos™ T211, or PPG 14 palmeth 60 hexyl dicarbamate, sold under the name Elfacos™ GT2125.

Mention may be made, as examples of emulsifying surfactants optionally present in the formulations for topical use in which said composition ($C_1$) or ($C_2$) can be incorporated, of nonionic surfactants, anionic surfactants or cationic surfactants.

Mention may be made, as examples of nonionic emulsifying surfactants optionally present in the formulations for topical use in which said composition ($C_1$) or ($C_2$) can be incorporated, of esters of fatty acids and of sorbitol, for example Montane™ 80, Montane™ 85 and Montane™ 60; alkyl polyglycosides and compositions of alkyl polyglycosides and of saturated or unsaturated and linear or branched fatty alcohols, the alkyl chain of said alkyl polyglycosides being composed of saturated or unsaturated and linear or branched alkyl groups, comprising from 14 to 22 carbon atoms, for example Montanov™, Easynov™ and Fluidanov™ products; esters of fatty acids and of polyglycerol, for example Isolan™ G134 and Plurol™ Diisostearique; ethoxylated castor oil and ethoxylated hydrogenated castor oil, Simulsol™989; compositions comprising glycerol stearate and ethoxylated stearic acid having between 5 mol and 150 mol of ethyleneoxide, for example the composition comprising ethoxylated stearic acid having 135 mol of ethylene oxide and glycerol stearate, sold under the name Simulsol™ 165; polyglycol or polyglycerol polyhydroxystearates, for example Hypermer™ B246 or Arlacel™ P135, Dehymuls™ PGPH or Decaglyn™ 5HS; polyethylene glycol-alkyl glycol copolymers, such as PEG-45 dodecyl glycol copolymer, such as Elfacos™ ST 9; ethoxylated sorbitan esters, for example Montanox™ products; mannitan esters; ethoxylated mannitan ethers; sucrose esters; or methyl glucoside esters.

Mention may be made, as examples of anionic emulsifying surfactants optionally present in the formulations for topical use in which said composition ($C_1$) or ($C_2$) can be incorporated, of decyl phosphate, cetyl phosphate, sold under the Amphisol™ name, glyceryl stearate citrate, cetearyl sulfate, the arachidyl/behenyl phosphates and arachidyl/behenyl alcohols composition sold under the name Sensanov™ WR, soaps, such as, for example, sodium stearate or triethanolammonium stearate, or salified amino acid N-acylated derivatives, such as, for example, stearoyl glutamate.

Mention may be made, as examples of cationic emulsifying surfactants optionally present in the formulations for topical use in which said composition ($C_1$) or ($C_2$) can be incorporated, of amine oxides, Quaternium™ 82 and the surfactants described in the international application published under the number WO 96/00719 and mainly those of which the fatty chain comprises at least 16 carbon atoms.

Mention may be made, as examples of opacifying and/or pearlescing agents optionally present in the formulations for topical use in which said composition ($C_1$) or ($C_2$) can be incorporated, of sodium palmitate, sodium stearate, sodium hydroxystearate, magnesium palmitate, magnesium stearate, magnesium hydroxystearate, ethylene glycol monostearate, ethylene glycol distearate, polyethylene glycol monostearate, polyethylene glycol distearate or fatty alcohols comprising from 12 to 22 carbon atoms.

Mention may be made, as examples of texturing agents optionally present in the formulations for topical use in which said composition ($C_1$) or ($C_2$) can be incorporated, of N-acylated derivatives of amino acids, for example the lauroyl lysine sold under the name Aminohope™ LL, the octenyl succinate starch sold under the Dryflo™ name, the myristyl polyglucoside sold under the name Montanov™ 14, cellulose fibers, cotton fibers, chitosan fibers, talc, sericite or mica.

Mention may be made, as examples of solvents and cosolvents optionally present in the formulations for topical use in which said composition ($C_1$) or ($C_2$) can be incorporated, of water, organic solvents, such as glycerol, diglycerol, glycerol oligomers, ethylene glycol, propylene glycol, butylene glycol, hexylene glycol, diethylene glycol, xylitol, erythritol, sorbitol or water-soluble alcohols, such as ethanol, isopropanol or butanol, or mixtures of water and of said organic solvents.

Mention may be made, as examples of oils optionally present in the formulations for topical use in which said composition ($C_1$) or ($C_2$) can be incorporated, of mineral oils, such as liquid paraffin, liquid petroleum jelly, isoparaffins or white mineral oils; oils of animal origin, such as squalene or squalane; vegetable oils, such as phytosqualane, sweet almond oil, coconut oil, castor oil, jojoba oil, olive oil, rapeseed oil, peanut oil, sunflower oil, wheatgerm oil, corn germ oil, soybean oil, cottonseed oil, alfalfa oil, poppy oil, pumpkinseed oil, evening primrose oil, millet oil, barley oil, rye oil, safflower oil, candlenut oil, passionflower oil, hazelnut oil, palm oil, shea butter, apricot kernel oil, calophylium oil, sisymbrium oil, avocado oil, calendula oil or oils resulting from flowers or vegetables; ethoxylated vegetable oils; synthetic oils, such as fatty acid esters, for example butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate, propylene glycol dicaprylate, esters derived from lanolic acid, such as isopropyl lanolate or isocetyl lanolate, fatty acid monoglycerides, diglycerides and triglycerides, such as glycerol triheptanoate, alkyl benzoates, hydrogenated oils, poly($\alpha$-olefin)s, polyolefins, such as polyisobutene, synthetic isoalkanes, such as isohexadecane or isododecane, or perfluorinated oils, or silicone oils, such as polydimethylsiloxanes, polymethylphenylsiloxanes, silicones modified by amines, silicones modified by fatty acids, silicones modified by alcohols, silicones modified by fatty acids and alcohols, silicones modified by polyether groups, epoxy-modified silicones, silicones modified by fluorinated groups, cyclic silicones and silicones modified by alkyl groups. "Oils" is understood to mean, in the present patent application, the water-insoluble compounds and/or the mixtures of water-insoluble compounds which exist under a liquid appearance at a temperature of 25° C.

Mention may be made, as examples of waxes optionally present in the formulations for topical use in which said composition ($C_1$) or ($C_2$) can be incorporated, of beeswax, carnauba wax, candelilla wax, ouricury wax, Japan wax, cork fiber wax, sugarcane wax, paraffin waxes, lignite waxes, microcrystalline waxes, lanolin wax, ozokerite, polyethylene wax, silicone waxes, vegetable waxes, fatty alcohols and fatty acids which are solid at ambient temperature, or glycerides which are solid at ambient temperature. "Waxes" is understood to mean, in the present patent application, the water-insoluble compounds and/or the mixtures of water-insoluble compounds which exist under a solid appearance at a temperature of greater than or equal to 45° C.

Mention may be made, as examples of fatty substances optionally present in the formulations for topical use in which said composition ($C_1$) or ($C_2$) can be incorporated, of saturated or unsaturated and linear or branched fatty alcohols comprising from 8 to 36 carbon atoms, or saturated or unsaturated and linear or branched fatty acids comprising from 8 to 36 carbon atoms.

Mention may be made, as examples of active principles optionally present in the formulations for topical use in which said composition ($C_1$) or ($C_2$) can be incorporated, of:

vitamins and their derivatives, in particular their esters, such as retinol (vitamin A) and its esters (retinyl palmitate, for example), ascorbic acid (vitamin C) and its esters, sugar derivatives of ascorbic acid (such as, for example, ascorbyl glucoside), tocopherol (vitamin E) and its esters (such as, for example, tocopherol acetate), or vitamins B3 or B10 (niacinamide and its derivatives);

compounds showing a lightening or depigmenting action on the skin, for example Sepiwhite™ MSH, arbutin, cojic acid, hydroquinone, Vegewhite™, Gatuline™, Synerlight™, Biowhite™, Phytolight™, Dermalight™, Clariskin™, Melaslow™, Dermawhite™, Ethioline™, Melarest™, Gigawhite™, Albatine™ or Lumiskin™;

compounds showing a soothing action, such as Sepicalm™ S, allantoin and bisabolol;

anti-inflammatory agents;

compounds showing a moisturizing action, such as, for example, urea, hydroxyureas, glycerol, polyglycerols, glycerol glucoside, diglycerol glucoside or polyglyceryl glucoside;

plant extracts rich in polyphenols, such as, for example, grape extracts, pine extracts, wine extracts or olive extracts;

compounds showing a slimming or lipolytic action, such as caffeine or its derivatives, Adiposlim™ or Adipoless™;

N-acylated proteins, N-acylated peptides, such as, for example, Matrixil™, N-acylated amino acids, partial hydrolysates of N-acylated proteins, amino acids, peptides, total hydrolysates of proteins, soybean extracts, for example Raffermine™, or wheat extracts, for example Tensine™ or Gliadine™;

plant extracts, such as plant extracts rich in tannins, plant extracts rich in isoflavones or plant extracts rich in terpenes;

extracts of freshwater or marine algae;

marine extracts in general, such as coral;

essential waxes, bacteria extracts, ceramides or phospholipids;

compounds showing an antimicrobial action or a purifying action, for example Lipacide™ C8G, Lipacide™ UG, Sepicontrol™ A5, Octopirox™ or Sensiva™ SC50;

compounds showing an energizing or stimulating property, such as Physiogenyl™, or panthenol and its derivatives, such as Sepicap™ MP;

antiaging active principles, such as Sepilift™ DPHP, Lipacide™ PVB, Sepivinol™, Sepivital™, Manoliva™, Phyto-Age™, Timecode™ or Survicode™;

antiphotoaging active principles;

active principles which protect the integrity of the dermoepidermal junction;

active principles which increase the synthesis of the components of the extracellular matrix, such as, for example, collagen, elastins or glycosaminoglycans;

active principles which act favorably on chemical cell communication, such as cytokines, or physical cell communication, such as integrins;

active principles which create a feeling of "heating" on the skin, such as activators of cutaneous microcirculation (such as, for example, nicotinic acid derivatives) or products which create a feeling of "coolness" on the skin (such as, for example, menthol and derivatives);

active principles which improve cutaneous microcirculation, for example venotonics, draining active principles or active principles having a decongestant purpose, such as, for example, extracts of ginko biloba, ivy, horse chestnut, bamboo, ruscus, butcher's broom, Centalla asiatica, fucus, rosemary or willow;

agents for tanning or browning the skin, such as, for example, dihydroxyacetone, isatin, alloxan, ninhydrin, glyceraldehyde, mesotartaric aldehyde, glutaraldehyde or erythrulose.

Mention may be made, as examples of thickening and/or gelling agents optionally present in the formulations for topical use in which said composition ($C_1$) or ($C_2$) can be incorporated, for example, of homopolymers or copolymers of acrylic acid or of acrylic acid derivatives, homopolymers or copolymers of acrylamide, homopolymers or copolymers of acrylamidomethylpropanesulfonic acid, of vinyl monomer or of trimethylammonioethylacrylate chloride, hydrocolloids of plant or biosynthetic origin, for example xanthan gum, karaya gum, carrageenates or alginates, galactomannans, such as, for example, tara gum, guar gum, fenugreek gum, locust bean gum or cassae gum, silicates, cellulose and its derivatives, starch and its hydrophilic derivatives, or polyurethanes.

Mention may more particularly be made, as examples of thickening and/or gelling agents optionally present in the formulations for topical use in which said composition ($C_1$) or ($C_2$) can be incorporated, of polymers of polyelectrolyte type, such as, for example, copolymers of acrylic acid and 2-methyl-2-[(1-oxo-2-propenyl)amino]-1-propanesulfonic acid (AMPS), copolymers of acrylamide and AMPS, copolymers of AMPS and 2-hydroxyethyl acrylate, AMPS homopolymer, acrylic acid homopolymer, copolymers of acryloyloxyethyltrimethylammonium chloride and acrylamide, copolymers of AMPS and vinylpyrrolidone, copolymers of acrylic acid and alkyl acrylates, the carbon-based chain of which comprises between ten and thirty carbon atoms, or copolymers of AMPS and alkyl acrylates, the carbon-based chain of which comprises between ten and thirty carbon atoms. Such polymers are sold under the names Simulgel™ EG, Sepigel™ 305, Simulgel™ 600, Simulgel™ NS, Simulgel™ INS 100, Simulgel™ FL, Simulgel™ A, Simulgel™ SMS 88, Sepinov™ EMT10, Sepiplus™ 400, Sepiplus™ 265, Sepiplus™ S and Sepimax™ ZEN.

Mention may be made, as examples of sunscreens optionally present in the formulations for topical use in which said composition ($C_1$) or ($C_2$) can be incorporated, of all those appearing in the Cosmetic Directive 76/768/EEC, amended, Annex VII.

The following experimental study illustrates the invention without, however, limiting it.

A) EXAMPLES OF THE PREPARATION OF COMPOSITION ($C_1$) ACCORDING TO THE PROCESS WHICH IS A SUBJECT MATTER OF THE INVENTION

Example 1: Preparation of a Composition ($E_1$) Based on Xylityl Glucosides which is Catalyzed by Hypophosphorous Acid 651.3 grams of xylitol, i.e. one molar equivalent, are introduced into a jacketed reactor, in which jacket a heat-exchange fluid circulates, provided with a stirrer. The xylitol is melted at 100° C. 230.4 grams of glucose, i.e. 0.3 mol equivalent, are gradually added to the reactor with stirring at 100° C.

7.8 grams of hypophosphorous acid as a 50% solution in water are subsequently added, i.e. a proportion by weight of 0.9% with respect to the sum of the weights of xylitol and glucose previously introduced.

The reaction medium is placed under a partial vacuum of $3 \times 10^4$ Pa (300 mbar) to $1.5 \times 10^4$ Pa (150 mbar) and maintained at 100° C.-105° C. for 5% hours, the water formed being removed by means of a distillation assembly. The reaction medium is subsequently cooled to a temperature of 95° C.-100° C. and neutralized by addition of 5.6 grams of 48% sodium hydroxide solution, in order to bring the pH of a 5% by weight solution of said mixture to 7.0. The composition ($E_1$) is thus obtained.

Example 2: Preparation of a Composition ($E_2$) Based on Xylityl Glucosides which is Catalyzed by Phosphoric Acid The procedure described in example 1 is employed with 526.7 grams of xylitol, i.e. one molar equivalent, and 187.3 grams of glucose, i.e. 0.3 mol equivalent, the hypophosphorous acid being replaced with 1.4 grams of phosphoric acid as a 75% by weight solution in water, i.e. a proportion by weight of 0.2% with respect to the sum of the weights of xylitol and glucose introduced. The composition ($E_2$) is thus obtained.

Example 3: Preparation of a Composition ($E_3$) Based on Sorbityl Glucosides which is Catalyzed by Hypophosphorous Acid 499.4 grams of sorbitol i.e. one molar equivalent, are introduced into a jacketed glass reactor, in which jacket a heat-exchange fluid circulates, provided with an efficient stirrer. The sorbitol is melted at 105° C.

987.4 grams of glucose, i.e. 2.0 mol equivalents, are gradually added to the reactor with stirring at 110° C.

2.98 grams of hypophosphorous acid as a 50% solution in water are added to the mixture thus obtained, i.e. a proportion by weight of 0.2% with respect to the sum of the weights of sorbitol and glucose previously introduced.

The reaction medium is placed under a partial vacuum of $2 \times 10^4$ Pa (200 mbar) to $4.6 \times 10^3$ Pa (46 mbar) and maintained at a temperature of 110° C.-130° C. for 4 hours, the water formed being removed by means of a distillation assembly. The reaction medium is subsequently cooled to a temperature of 95° C.-100° C. and neutralized by addition of 2.7 grams of 48% sodium hydroxide solution, in order to bring the pH of a 5% by weight solution of said mixture to 7.0. The composition ($E_3$) is thus obtained.

Example 4: Preparation of a Composition ($E_4$) Based on Xylityl Glucosides which is Catalyzed by Polyphosphoric Acid The procedure described in example 1 is employed with 500.2 grams of xylitol, i.e. one molar equivalent, and 177.8 grams of glucose, i.e. 0.3 mol equivalent, the hypophosphorous acid being replaced with 0.91 gram of 117% polyphosphoric acid, i.e. a proportion by weight of 0.13% with respect to the sum of the weights of xylitol and glucose introduced. The composition ($E_4$) is thus obtained.

B) EXAMPLES OF THE PREPARATION OF COMPOSITIONS ACCORDING TO PROCESSES OF THE STATE OF THE ART (COMPARATIVE EXAMPLES)

Example A: Preparation of a Composition ($E_A$) Based on Xylityl Glucosides which is Catalyzed by Sulfuric Acid The procedure described in example 1 is employed with 621.4 grams of xylitol, i.e. one molar equivalent, and 220.8 grams of glucose, i.e. 0.3 mol equivalent, the hypophosphorous acid being replaced with 1.7 gram of 98% by weight sulfuric acid in water, i.e. a proportion by weight of 0.2% with respect to the sum of the weights of xylitol and glucose introduced. The composition ($E_A$) is obtained.

Example B: Preparation of a Composition ($E_B$) Based on Xylityl Glucosides which is Catalyzed by Methanesulfonic Acid The procedure described in example 1 is employed with 500.6 grams of xylitol, i.e. one molar equivalent, and 177.6 grams of glucose, i.e. 0.3 mol equivalent, the hypophosphorous acid being replaced with 1.4 grams of methanesulfonic acid, i.e. a proportion by weight of 0.2% with respect to the sum of the weights of xylitol and glucose introduced. The composition ($E_B$) is obtained.

Example C: Preparation of a Composition ($E_C$) Based on Xylityl Glucosides which is Catalyzed by Boron Trifluoride in Ethyl Ether ($BF_3.EtO_2$)

The procedure described in example 1 is employed with 585.8 grams of xylitol, i.e. one molar equivalent, and 207.5 grams of glucose, i.e. 0.3 mol equivalent, the hypophosphorous acid being replaced with 3.9 grams of 48% by weight boron trifluoride in ethyl ether ($BF_3.EtO_2$), i.e. a proportion by weight of 0.5% with respect to the sum of the weights of xylitol and glucose introduced. The composition ($E_C$) is obtained.

Example D: Preparation of a Composition ($E_D$) Based on Xylityl Glucosides which is Catalyzed by a Mixture of Sulfuric Acid and Hypophosphorous Acid The procedure described in example 1 is employed with 134.3 grams of xylitol, i.e. one molar equivalent, and 52.7 grams of glucose, i.e. 0.3 mol equivalent, the hypophosphorous acid being replaced with a mixture of 0.41 grams of 98% sulfuric acid in water (i.e. a proportion by weight of 0.22% with respect to the sum of the weights of xylitol and glucose introduced) and 0.96 gram of 50% by weight hypophosphorous acid in water (i.e. a proportion by weight of 0.5% with respect to the sum of the weights of xylitol and glucose introduced). The composition ($E_D$) is obtained.

Example E: Preparation of a Composition ($E_E$) Based on Sorbityl Glucosides which is Catalyzed by a Sulfuric Acid According to a Process of the State of the Art The procedure described in example 1 is employed with 528.1 grams of sorbitol, i.e. one molar equivalent, and 1051.1 grams of glucose, i.e. 2.0 mol equivalents, the hypophosphorous acid being replaced with 3.0 grams of 98% sulfuric acid in water, i.e. a proportion by weight of 0.2% with respect to the sum of the weights of sorbitol and glucose introduced. The procedure employed makes it possible to obtain the composition ($E_E$).

C) CHARACTERIZATION OF THE COMPOSITIONS ($E_1$), ($E_2$), ($E_4$), ($E_A$), ($E_B$), ($E_C$) AND ($E_D$)

The compositions ($E_1$), ($E_2$) and ($E_4$) obtained by the process according to the invention and the compositions ($E_A$), ($E_B$), ($E_C$) and ($E_D$) obtained according to processes of the state of the art were analyzed, in order to determine the content by weight of the various compounds constituting them, by means of a gas chromatograph provided with an HT-SimDist™ CB metal column (PE Chropack™), 10 m×0.53 mm ID, film thickness at 0.5 µm, with helium as carrier gas and equipped with a detector of FID type. The results obtained are recorded in table 1 below.

TABLE 1

|  | ($E_1$) | ($E_2$) | ($E_4$) | ($E_A$) | ($E_B$) | ($E_C$) | ($E_D$) |
| --- | --- | --- | --- | --- | --- | --- | --- |
| Xylitol | 59.1% | 57.1% | 57.6% | 26.0% | 33.3% | 43.7% | 17.7% |
| 1,4-Anhydroxylitol[1] | 2.4% | 0.6% | 1.2% | 32.2% | 22.9% | 17.2% | 37.6% |
| Xylityl glucosides | 38.5% | 42.3% | 41.2% | 41.8% | 43.8% | 39.1% | 44.7% |
| Mean degree of polymerization (x) | 1.26 | 1.26 | 1.26 | 1.46 | 1.32 | 1.29 | 1.42 |

[1]1,4-Anhydroxylitol corresponds to the dehydration product of xylitol of formula ($B_{12}$).

D) CHARACTERIZATION OF THE COMPOSITIONS ($E_3$) AND ($E_E$)

The composition ($E_3$) obtained by the process according to the invention and the composition ($E_E$) obtained according to a process of the state of the art were analyzed, in order to determine the content by weight of the various compounds constituting them, by means of a gas chromatograph provided with an HT-SimDist™ CB metal column (PE Chropack™) 10 m×0.53 mm ID, film thickness of 0.5 μm, with helium as carrier gas and equipped with a detector of FID type. The results obtained are recorded in table 2 below.

TABLE 2

|  | ($E_3$) | ($E_E$) |
|---|---|---|
| Sorbitol | 10.1% | 0.1% |
| Sorbitan[(2)] | 1.7% | 16.9% |
| Isosorbide[(3)] | 0.1% | 14.4% |
| Sorbityl glucosides | 88.1% | 68.6% |
| Mean degree of polymerization (x) | 2.15 | 2.10 |

[(2)]1,4-Anhydrosorbitol corresponds to the dehydration product of sorbitol of formula ($B_{13}$).
[(3)]Isosorbide corresponds to the dehydration product of 1,4-anhydrosorbitol of formula ($B_{14}$).

E) ANALYSIS OF AND COMMENTS ON THE RESULTS

The analyses carried out for the compositions ($E_1$), ($E_2$) and ($E_4$), resulting from the implementation of the process according to the invention and respectively involving hypophosphorous acid, phosphoric acid and polyphosphoric acid as reaction catalyst, show a content of 1,4-anhydroxylitol, the substance of formula ($B_{12}$) as defined above, resulting from the dehydration of xylitol, respectively of 2.4% for the composition ($E_1$), of 0.6% for the composition ($E_2$) and of 1.2% for the composition ($E_4$). The compositions ($E_A$), ($E_B$), ($E_C$) and ($E_D$) are characterized by contents of 1,4-anhydroxylitol respectively equal to 32.2%, 22.9%, 17.2% and 37.6%.

The analyses carried out show that the composition ($E_3$), resulting from the implementation of the process according to the invention involving hypophosphorous acid as reaction catalyst, is characterized by a total content of dehydrated sorbitol entities of 1.8%, whereas the composition ($E_E$), obtained by the implementation of a process involving sulfuric acid as reaction catalyst, comprises a total content of dehydrated sorbitol entities equal to 31.3%.

The processes according to the invention, employing an acid catalyst chosen from hypophosphorous acid, phosphoric acid and polyphosphoric acid during the acetalization reaction of a reducing sugar with a polyol of formula ($A_1$) as defined above, thus make it possible to prepare compositions based on polyol glycosides of formula (I) with a restricted amount of byproducts from the dehydration of the polyol of formula ($A_1$).

F) FORMULATIONS

In the following formulations, the percentages are expressed by weight of the formulation.

F.1 Face Makeup-Removing Fluid
Formulation

| | | |
|---|---|---|
| | Composition ($E_1$) | 10.00% |
| | Methylparaben | 0.15% |
| | Phenoxyethanol | 0.80% |
| | SEPICALM ™ S | 1.00% |
| | Fragrance/Scent | 0.10% |
| | Water | q.s. 100.00% |

Procedure: The various ingredients are mixed in water with magnetic stirring in the order shown and the pH is adjusted to the vicinity of 7.

F.2 Hair and Body Shampoo for Children
Formulation

| | | |
|---|---|---|
| A | Composition ($E_1$) | 15.00% |
| | Proteol ™ APL | 5.00% |
| | Sepicide ™ HB | 0.50% |
| | Fragrance/Scent | 0.10% |
| B | Water | 20.00% |
| | Capigel ™ 98 | 3.50% |
| C | Water | q.s. 100.00% |
| | Sepicide ™ CI | 0.30% |
| | Colorant | q.s. |
| | Sodium hydroxide | q.s. pH = 7.2 |

Procedure: The composition ($E_1$) is mixed with the Proteol™ APL and the Sepicide™ HB (phase A). The Capigel™ 98 is diluted in a portion of the water and added to the phase A obtained above (phase B). The remaining water is added to the phase B, followed by the Sepicide™ CI and the colorant. The pH of the mixture is adjusted to approximately 7.2 with sodium hydroxide.

F.3 Makeup-Removing Wipes for the Eyes
Formulation

| | | |
|---|---|---|
| A | Composition ($E_1$) | 3.00% |
| B | Sepicide ™ HB2 | 0.50% |
| C | Sepicalm ™ VG | 0.50% |
| | Glycerol | 10.00% |
| | Fragrance/Scent | 0.05% |
| D | Water | q.s. 100.00% |

Procedure: The ingredients of the phase B and also of the phase C are mixed in the phase A until the solution is clear. The phase D is added.

F.4 Mild Foaming Gel
Formulation

| | | |
|---|---|---|
| A | Composition ($E_2$) | 8.50% |
| | Proteol ™ APL | 3.00% |
| | Euxyl ™ PE 9010 | 1.00% |
| | Fragrance/Scent | 0.10% |
| B | Water | q.s. 100.00% |
| | Lactic acid | q.s. pH = 6.0 |

Procedure: The fragrance and the preservative Euxyl™ PE 9010 are dissolved in the mixture composed of the composition ($E_2$) and of Proteol™ APL (phase A). The water is added and the pH is adjusted to approximately 6.0 with lactic acid.

F.5 Shampoo for Frequent Use
Formulation

| | | |
|---|---|---|
| A | Composition ($E_2$) | 12.80% |
| | Proteol ™ OAT | 5.00% |
| | Euxyl ™ PE 9010 | 1.00% |

|   |   |   |
|---|---|---|
|   | Fragrance/Scent | 0.30% |
|   | Water | q.s. 100.00% |
| B | Montaline ™ C40 | 8.50% |
|   | Lactic acid | q.s. pH = 6.0 |

Procedure: All the ingredients of the phase A are mixed and, after homogenization, the Montaline™ C40 is added and the pH is adjusted to approximately 6.0 using lactic acid.

F.6 Ultramild Shampoo for Babies

Formulation

|   |   |   |
|---|---|---|
| A | Composition (E$_3$) | 10.00% |
|   | Amisoft ™ CS-11 | 4.00% |
|   | Fragrance/Scent | 0.10% |
|   | Sepicide ™ HB | 0.30% |
|   | Sepicide ™ CI | 0.20% |
|   | Water | q.s. 100.00% |
| B | Water | 20.00% |
|   | CAPIGEL ™ 98 | 3.50% |
|   | Tromethamine | q.s. pH = 7.2 |

Procedure: All the ingredients of the phase A are mixed in the order shown until a clear phase A is obtained. The Capigel™ 98 is separately added to the water, then this phase B, thus prepared, is added to the phase A and the pH is adjusted to 7.2 using tromethamine.

F.7 Cleansing milk for babies

Formulation

|   |   |   |
|---|---|---|
| A | Simulsol ™ 165 | 2.00% |
|   | Montanov ™ 202 | 1.00% |
|   | Lanol ™ 99 | 3.00% |
|   | Dimethicone | 1.00% |
|   | Isohexadecane | 3.00% |
| B | Water | q.s. 100.00% |
| C | Sepiplus ™ 400 | 0.30% |
| D | Composition (E$_1$) | 6.35% |
| E | Sepicide ™ HB | 0.30% |
|   | DMDM Hydantoin | 0.20% |
|   | Fragrance/Scent | 0.10% |

Procedure: The phases A and B, formed by mixing the various constituents, are heated separately. The phase C is added to the hot fatty phase and the emulsion is produced by running in the aqueous phase; the mixture is homogenized for a few minutes with vigorous stirring (via a rotor/stator turbine). The phase D is then added to the hot emulsion, which is cooled with moderate stirring until it has returned to ambient temperature. The phase E is added at 40° C.

F.8 Cleansing Powder Lotion for Sensitive Skin

Formulation

|   |   |   |
|---|---|---|
| A | Lipacide ™ C8G | 0.95% |
|   | Methylparaben | 0.10% |
|   | Ethylparaben | 0.024% |
|   | Propylparaben | 0.0119% |
|   | Butylparaben | 0.024% |
|   | Isobutylparaben | 0.0119% |
|   | Water | 20.00% |
|   | Disodium EDTA | 0.10% |
|   | Triethanolamine | 1.38% |
| B | Composition (E$_2$) | 1.80% |
|   | Fragrance/Scent | 0.10% |
| C | Sepicalm ™ S | 0.28% |
|   | Water | q.s. 100.00% |
|   | Lactic acid | q.s. pH = 5.2 |
| D | Micropearl ™ M310 | 5.00% |

Procedure: The ingredients of the phase A are dissolved in water at 80° C. The fragrance is dissolved separately in the composition (E$_2$) to prepare the phase B. The cooled phase A is added to the phase B and then the Sepicalm™ S and the remaining water are introduced. The final pH is checked and optionally adjusted to approximately 5.2. The Micropearl™ M310 is then added.

F.9 Shower Gel for Children

Formulation

|   |   |   |
|---|---|---|
| A | Water | 56.06% |
|   | Sepimax ™ Zen | 3.00% |
|   | Sepiplus ™ S | 0.80% |
| B | Proteol ™ OAT | 20.80% |
|   | Oramix ™ NS 10 | 9.30% |
|   | Amonyl ™ 265 BA | 5.10% |
| C | Composition (E$_1$) | 2.00% |
|   | Glyceryl glucoside | 1.00% |
|   | Phenoxyethanol & Ethylhexylglycerin | 1.00% |
|   | Fragrance/Scent | 0.90% |
|   | Colorant | 0.04% |

Procedure: The Sepimax™ Zen is dispersed in the water and stirring is carried out using a mechanical stirrer provided with a deflocculator, a counter propeller and a paddle of anchor type, until a perfectly smooth gel is obtained. The Sepiplus™ S is added and then stirring is carried out until the mixture is homogenous. The ingredients of the phase B are subsequently added, the mixture is homogenized and the additives of the phase C are added individually. The pH is adjusted to 6.0-6.5.

F.10 BB Cream

Formulation

|   |   |   |
|---|---|---|
| A | Easynov ™ | 2.30% |
|   | Lanol ™ 99 | 1.00% |
|   | Sepimat ™ H10W | 1.00% |
|   | Ethylhexyl methoxycinnamate | 5.00% |
| B | Cyclomethicone | 6.00% |
|   | Triethoxycaprylylsilane & Alumina-silane & Titanium oxide | 8.00% |
|   | Iron oxide red & Triethoxycaprylylsilane | 0.24% |
|   | Iron oxide yellow & Triethoxycaprylylsilane | 0.66% |
|   | Iron oxide black & Triethoxycaprylylsilane | 0.09% |
|   | Fragrance/Scent | 0.10% |
| C | Water | q.s. 100% |
|   | Glycerol | 6.00% |
|   | Sepinov ™ EMT10 | 1.20% |
| D | Composition (E$_1$) | 2.00% |
|   | Sepitonic ™ M3 | 1.00% |
|   | Phenoxyethanol & Ethylhexylglycerin | 1.00% |

Procedure: The phase B is prepared by mixing the various ingredients and the mixture is homogenized using a mixer provided with a rotor-stator system at a rotational speed of 4500 revolutions per minute, for a period of time of 6 minutes. The phase C is prepared by adding the Sepinov™ EMT10 to the mixture of water and glycerol and the mixture is homogenized using a mixer provided with a rotor-stator system at a rotational speed of 4000 revolutions per minute for 4 minutes. The phases A and B are added to the phase C and the resulting mixture is stirred using a mechanical stirrer provided with a paddle of anchor type, at a speed of 30 revolutions per minute for 2 minutes and then at a speed of 50 revolutions per minute for 20 minutes. The components of the phase D are added one by one and the mixture is stirred at a speed of 50 revolutions per minute for 25 minutes.

F.11 High-Protection Sun Spray, SPF Greater than 30 Formulation

| A | Montanov ™ L | 1.00% |
|---|---|---|
|   | Montanov ™ 82 | 1.00% |
|   | C12-15 Alkyl benzoate | 17.00% |
|   | Dimethicone | 3.00% |
|   | Octocrylene | 6.00% |
|   | Ethylhexyl methoxycinnamate | 6.00% |
|   | Bis-ethylhexyloxyphenol Methoxyphenyl Triazine | 3.00% |
|   | Tocopherol | 0.05% |
| B | Water | q.s. 100% |
| C | Simulgel ™ INS 100 | 0.50% |
|   | Cyclodimethicone | 5.00% |
| D | Composition ($E_1$) | 3.00% |
|   | Phenoxyethanol & Ethylhexylglycerin | 1.00% |
|   | Fragrance/Scent | 0.20% |
| E | Methylene Bis-Benzotriazolyl Tetramethylbutylphenol | 10.00% |
|   | Citric acid, 25% | q.s. pH = 5 |

Sepicalm™ S: Mixture of N-cocoylamino acids, of sarcosine, of potassium aspartate and of magnesium aspartate as described in WO 98/09611, sold by Seppic.
Proteol™ APL: Mixture of sodium salts of N-cocoylamino acids which are obtained by acylation of the characteristic amino acids of apple juice, sold by Seppic.
Sepicide™ HB, a mixture of phenoxyethanol, of methylparaben, of ethylparaben, of propylparaben and of butylparaben, is a preservative, sold by Seppic.
Capigel™ 98 is a copolymer of acrylates, sold by Seppic.
Sepicide™ CI, imidazoline urea, is a preservative, sold by Seppic.
Sepicide™ HB, a mixture of phenoxyethanol, methylparaben, ethylparaben, propylparaben, butylparaben and isobutylparaben, is a preservative, sold by Seppic.
Sepicalm™ VG is a mixture of N-palmitoylproline in sodium salt form and of extract of flowers of *Nymphaea alba*, sold by Seppic.
Euxyl™ PE 9010, a mixture of phenoxyethanol and of Ethylhexylglycerin, is a preservative sold by Seppic.
Proteol™ OAT is a mixture of N-lauroylamino acids obtained by complete hydrolysis of oat protein, as described in WO 94/26694, sold by Seppic.
Montaline™ C40 is a monoethanolamine cocamidopropyl betainamide chloride salt.
Amisoft™ CS-11 is a disodium salt of N-cocoylglutamate, sold by Ajinomoto.
Simulsol™ 165 is a mixture of PEG-100 stearate and of glyceryl stearate, sold by Seppic.
Montanov™ 202 (arachidyl alcohol, behenyl alcohol and arachidyl glucoside) is a self-emulsifiable composition, such as those described in EP 0 977 626, sold by Seppic.
Lanol™ 99 is isononyl isononanoate, sold by Seppic.
Sepiplus™ 400 is a self-invertible inverse latex of polyacrylates in polyisobutene which comprises polysorbate 20, such as described in WO 2005/040230, sold by Seppic.
Lipacide™ C8G is capryloyl glycine, sold by Seppic.
Micropearl™ M310 is a crosslinked polymethyl methacrylate polymer which is provided in powder form and which is used as texture modifier.
Sepimax™ Zen (INCI name: Polyacrylate Crosspolymer-6) is a thickening polymer which is provided in the form of a powder, sold by Seppic.
Sepiplus™ S (INCI name: Hydroxyethyl Acrylate/Sodium Acryloyldimethyl Taurate Copolymer & Polyisobutene & PEG-7 Trimethylolpropane Coconut Ether) is a self-invertible inverse latex used as thickening agent, sold by Seppic.
Amonyl™ 265 BA (INCI name: Cocobetaine) is a foaming amphoteric surface-active agent, sold by Seppic.
Sepinov™ EMT10 (INCI name: Hydroxyethyl Acrylate/Sodium Acryloyldimethyl Taurate Copolymer) is a thickening copolymer which is provided in the form of a powder, sold by Seppic.
Easynov™ (INCI name: Octyldodecanol and Octyldodecyl Xyloside and PEG-30 Dipolyhydroxystearate) is an emulsifying agent having a lipophilic tendency, sold by Seppic.
Sepimat™ H10 FW (INCI name: Methyl Methacrylate Crosspolymer and Squalane) is a polymer used as texturing agent, sold by Seppic.
Sepitonic™ M3 (INCI name: Magnesium Aspartate and Zinc Gluconate and Copper Gluconate) is a mixture used as energizing ingredient for cells and an agent for combating free radicals.
Montanov™ L (INCI name: C14-22 Alcohols and C12-20 Alkylglucoside) is an emulsifying agent, sold by Seppic.
Montanov™ 82 (INCI name: Cetearyl Alcohol and Coco-glucoside) is an emulsifying agent, sold by Seppic.
Simulgel™ INS100 (INCI name: Hydroxyethyl Acrylate/Sodium Acryloyldimethyl Taurate Copolymer and Isohexadecane and Polysorbate 60) is a polymeric thickening agent which is provided in the form of an inverse latex, sold by Seppic.

The invention claimed is:
1. A process for preparing a composition ($C_2$), said composition ($C_2$) comprising, per 100% of its weight:
from 1% to 70% by weight of a polyol of formula ($A_1$):

$$HO-CH_2-(CHOH)_n-CH_2-OH \qquad (A_1)$$

in which n is an integer equal to 2, 3 or 4;
from 25% to 98.9% by weight of a composition ($C_1$) represented by the formula (I):

$$HO-CH_2-(CHOH)_n-CH_2-O-(G)_x-H \qquad (I)$$

in which G represents the residue of a reducing sugar selected from the residues of glucose, xylose and arabinose, n is an integer equal to 2, 3 or 4 and x, which indicates the mean degree of polymerization of said residue G, represents a decimal number of greater than 1 and less than or equal to 5;
from 0.1% to 2.4% by weight of a compound (B) or of a mixture of compounds (B) chosen from:
the compound of formula ($B_{11}$):

the compound of formula ($B_{12}$):

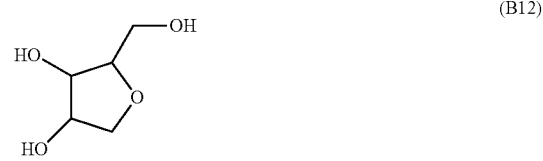

the compound of formula ($B_{13}$):

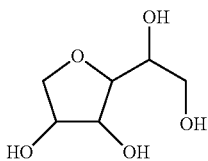
(B13)

and the compound of formula ($B_{14}$):

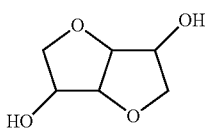
(B14)

said process comprising at least one stage a) of reaction of a polyol of formula ($A_1$):

(A₁)

in which n is an integer equal to 2, 3 or 4, with a reducing sugar of formula (II):

(II)

in which G represents the residue of a reducing sugar, in the presence of an acid catalyst ($C_a$);

wherein said acid catalyst ($C_a$) is chosen from hypophosphorous acid, phosphoric acid and polyphosphoric acid;

wherein, in stage a), the molar ratio, of a reducing sugar of formula (II) to polyol of formula ($A_1$), is greater than or equal to 1/3 and less than or equal to 4/1; and wherein, in stage a), the proportion by weight of acid catalyst ($C_a$) employed is greater than or equal to 0.05% and less than or equal to 2% per 100% of the sum of the weights of a reducing sugar of formula (II) and of polyol of formula ($A_1$).

2. The process according to claim 1, wherein, in the formula (I), x represents a decimal number greater than or equal to 1.05 and less than 3.

3. The process according to claim 1, wherein, in stage a), the acid catalyst ($C_a$) employed is hypophosphorous acid.

4. The process according to claim 1, wherein, in stage a), the acid catalyst ($C_a$) employed is phosphoric acid.

5. The process according to claim 1, wherein:
in the formula ($A_1$), n is an integer equal to 2,
in the formula (I), n is an integer equal to 2, said residue G of a reducing sugar represents the residue of glucose and x represents a decimal number of between 1.05 and 2.5, and
the compound (B) is the compound of formula ($B_{11}$).

6. The process according to claim 1, wherein:
in the formula ($A_1$), n is an integer equal to 3,
in the formula (I), n is an integer equal to 3, said residue G of a reducing sugar represents the residue of glucose and x represents a decimal number of between 1.05 and 2.5, and
the compound (B) is the compound of formula ($B_{12}$).

7. The process according to claim 1, wherein:
in the formula ($A_1$), n is an integer equal to 4,
in the formula (I), n is an integer equal to 4, said residue G of a reducing sugar represents the residue of glucose and x represents a decimal number of between 1.05 and 2.5, and
the compound (B) is a mixture of the compound of formula ($B_{13}$) and the compound ($B_{14}$).

8. The process according to claim 1 wherein said acid catalyst ($C_a$) is polyphosphoric acid.

* * * * *